United States Patent
Dhuppad et al.

(10) Patent No.: US 10,632,108 B2
(45) Date of Patent: *Apr. 28, 2020

(54) TIOTROPIUM INHALATION SOLUTION FOR NEBULIZATION

(71) Applicant: Glenmark Specialty S.A., La Chaux-de-Fonds (CH)

(72) Inventors: Ulhas R. Dhuppad, Nashik (IN); Franciscus Koppenhagen, Deerfield Beach, FL (US); Sunil Chaudhari, Nashik (IN); Suresh Rajurkar, Nashik (IN); Chandrakant Dhatrak, Nashik (IN); Alkesh Kasliwal, Nanded (IN)

(73) Assignee: GLENMARK SPECIALTY S.A., La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,738

(22) Filed: May 7, 2018

(65) Prior Publication Data

US 2019/0105306 A1    Apr. 11, 2019

Related U.S. Application Data

(63) Continuation of application No. 15/663,246, filed on Jul. 28, 2017, now Pat. No. 9,987,260, which is a continuation-in-part of application No. 15/157,143, filed on May 17, 2016, now Pat. No. 9,757,365.

(30) Foreign Application Priority Data

May 18, 2015    (IN) .......................... 1945/MUM/2015

(51) Int. Cl.
| | |
|---|---|
| *A61K 31/435* | (2006.01) |
| *A61K 31/439* | (2006.01) |
| *A61K 47/18* | (2017.01) |
| *A61K 47/02* | (2006.01) |
| *A61K 9/00* | (2006.01) |
| *A61P 11/08* | (2006.01) |

(52) U.S. Cl.
CPC .......... *A61K 31/439* (2013.01); *A61K 9/0078* (2013.01); *A61K 47/02* (2013.01); *A61K 47/183* (2013.01); *A61P 11/08* (2018.01)

(58) Field of Classification Search
CPC ........................... C07D 487/06; A61K 31/435
USPC ....................................................... 514/291
See application file for complete search history.

(56) References Cited

U.S. PATENT DOCUMENTS

| | | | |
|---|---|---|---|
| 6,777,423 B2 | 8/2004 | Banholzer et al. | |
| RE39,820 E | 9/2007 | Banholzer et al. | |
| 9,757,365 B2 | 9/2017 | Dhuppad et al. | |
| 9,987,260 B2 * | 6/2018 | Dhuppad | ............... A61P 11/08 |
| 2002/0111363 A1 | 8/2002 | Drechsel et al. | |
| 2002/0189610 A1 | 12/2002 | Bozung et al. | |
| 2003/0149007 A1 | 8/2003 | Chaudry et al. | |
| 2003/0215396 A1 | 11/2003 | Freund et al. | |
| 2004/0019073 A1 | 1/2004 | Drechsel et al. | |
| 2004/0132761 A1 | 7/2004 | Drechsel et al. | |
| 2004/0192675 A1 | 9/2004 | Pairet et al. | |
| 2005/0058606 A1 | 3/2005 | Six et al. | |
| 2005/0175544 A1 | 8/2005 | Chaudry et al. | |

FOREIGN PATENT DOCUMENTS

WO    WO-2016178019 A1    11/2016

OTHER PUBLICATIONS

Spiriva® Respimat® (tiotropium bromide) Inhalation Spray for Oral Inhalation, prescribing information, 2004.
Wang Wei, et al., Preparation and In Vitro Evaluation of Tiotropium Bromide Inhalation Solution, Chinese Journal of Pharmaceuticals, 2012, 43:4.
Mutlu, et al., Laryngospasm and Paradoxical Bronchoconstriction After Repeated Doses of ?2-Agonists Containing Edetate Disodium, Mayo Clin Proc, 2000, 75:285-287.

* cited by examiner

*Primary Examiner* — Raymond J Henley, III
(74) *Attorney, Agent, or Firm* — Blank Rome LLP

(57) ABSTRACT

The present invention relates to a sterile pharmaceutical composition comprising tiotropium or a pharmaceutically acceptable salt thereof, for inhalation via nebulization to a subject (e.g. a human). The invention also relates to a process for preparing the pharmaceutical composition and its use in the treatment of respiratory diseases such as chronic obstructive pulmonary disease (COPD) in a subject.

20 Claims, No Drawings

TIOTROPIUM INHALATION SOLUTION FOR NEBULIZATION

RELATED APPLICATIONS

This patent application is a continuation of U.S. patent application Ser. No. 15/663,246, filed Jul. 28, 2017, now U.S. Pat. No. 9,987,260, which is a continuation-in-part of U.S. patent application Ser. No. 15/157,143, filed May 17, 2016, now U.S. Pat. No. 9,757,365, which claims priority to Indian Provisional Application number 1954/MUM/2015 filed on May 18, 2015, each of which is hereby incorporated by reference.

FIELD OF THE INVENTION

The present invention relates to a sterile pharmaceutical composition comprising tiotropium or a pharmaceutically acceptable salt thereof, for inhalation via nebulization to a subject (e.g. a human). The invention also relates to a process for preparing the pharmaceutical composition and its use in the treatment of respiratory diseases such as chronic obstructive pulmonary disease (COPD) in a subject.

BACKGROUND OF THE INVENTION

Anticholinergic agents are believed to inhibit vagally-mediated reflexes by blocking acetylcholine at the cholinergic receptor. Anticholinergic agents are also believed to inhibit secretions of the serous and sero-mucous glands of the nasal mucosa. Anticholinergic agents for the treatment or control of respiratory disorders include tiotropium, oxitropium, ipratropium, glycopyrrolate, aclidinium, and salts thereof.

One known anticholinergic agent is tiotropium bromide, the chemical name of which is (1α, 2β, 4β, 5α, 7β)-7-[(hydroxydi-2-thienylacetyl) oxy]-9, 9-dimethyl-3-oxa-9-azoniatricyclo [3.3.1.02, 4] nonane bromide monohydrate. Tiotropium bromide is commercially marketed in the United States by Boehringer Ingelheim Pharmaceuticals, Inc. as SPIRIVA® capsules containing lactose and 18 µg tiotropium (equivalent to 22.5 µg tiotropium bromide monohydrate) and inhalation solution SPIRIVA® RESPIMAT containing tiotropium bromide, water for injection, edetate disodium, benzalkonium chloride and hydrochloric acid. Tiotropium bromide is indicated for the maintenance treatment of bronchospasm associated with COPD and for reducing COPD exacerbations.

US 2004/0019073 discloses an aqueous inhalation solution comprising tiotropium and the preservative benzalkonium chloride.

Inhalation solutions generally contain preservatives such as benzalkonium chloride. Frequent exposure to low concentrations of benzalkonium chloride may lead to adverse effects. Some studies (Beasley et al., 1987, *British Medical Journal*, Vol 294, 1197-1198; Beasley et al., 1988, *Br. J. Clin. Pharmac.* 25, 283-287; Miszkiel et al., 1988, *Br. J. Clin. Pharmac.* 25, 157-163) also suggest that repeated use of COPD treatments with benzalkonium chloride may result in paradoxic bronchoconstriction, as benzalkonium chloride has bronchoconstrictor properties 7.4 times less potent than histamine. Moreover, exposure to benzalkonium chloride may lead to occupational asthma and may also cause dose-dependent bronchoconstriction.

Treatments for COPD often come in multiple dosage units and must be diluted to specific concentrations suitable for treating patients, or be directly delivered with the help of a costly and complicated device. This poses several problems while preparing the final dose and/or device for delivery. For example, COPD treatments requiring administration of a single dose unit from multiple dosage units sometimes lack proper mixing or diluting instructions, or the instructions for preparing and using the COPD treatment may be hard to follow or can be easily lost. Of even greater concern is haphazard diluting or mixing of COPD medications, which can result in administering the wrong dosage. This could be especially harmful for patients those are less tolerant to higher dosages of asthma medications. Incorrect mixing can also result in treatment failure such that additional medical attention is required, thereby increasing the time, expense and personnel costs associated with therapy.

There is, therefore, a need for an improved inhalation solution, system, kit and method for relieving symptoms associated with COPD.

SUMMARY OF THE INVENTION

The present invention relates to a sterile pharmaceutical composition for inhalation via nebulization to a patient (e.g., a human). The pharmaceutical composition comprises tiotropium or its salt (e.g., a pharmaceutically acceptable salt) and water. The pharmaceutical composition may be a solution. The pharmaceutical composition may be contained within a container suitable for nebulization. The pharmaceutical composition may be administered in nebulized form to relieve bronchospasm in patients suffering from COPD or for reducing COPD exacerbations.

In one embodiment a sterile pharmaceutical composition is a unit dose nebulizable pharmaceutical solution for inhalation comprising tiotropium or its salt. The pharmaceutical solution may be administered in nebulized form to relieve bronchospasm in a subject, such as a subject suffering from COPD.

In a preferred embodiment, the pharmaceutical composition or solution is free, or substantially free, of preservative including, but not limited to, quaternary ammonium preservatives, such as a benzalkonium salt, (e.g., benzalkonium chloride). For example, the pharmaceutical composition or solution may contain less than about 0.1% by weight of preservative (or quaternary ammonium preservative) (such as less than about 0.05%, less than about 0.02%, or less than about 0.008%), based on 100% total weight of composition or solution.

Yet another embodiment is a sterile, unit dose nebulizable pharmaceutical solution for inhalation comprising tiotropium or its salt wherein the composition is free, or substantially free, of complexing agent (such as ethylene diamine tetra-acetic acid (EDTA). For example, the pharmaceutical composition or solution may contain less than about 0.1% by weight of complexing agent (such as less than about 0.05%, less than about 0.02%, or less than about 0.008%), based on total weight of composition or solution.

One embodiment is a pharmaceutical composition comprising
(i) tiotropium or its pharmaceutically acceptable salts thereof
(ii) water
wherein said composition is free of preservative and complexing agent.

Yet another embodiment is a sterile nebulizable pharmaceutical solution for inhalation via nebulization comprising tiotropium or its salt, wherein the composition is free, or substantially free, of (a) EDTA or a salt thereof and (b) a benzalkonium salt, such as benzalkonium chloride.

In a preferred embodiment, the tiotropium salt in the pharmaceutical composition or pharmaceutical solution described herein is tiotropium bromide, such as tiotropium bromide monohydrate ((1α,2β,4β,7β)-7-[(hydroxydi-2-thienylacetyl)oxy]-9,9-dimethyl-3-oxa-9-azoniatricyclo [3.3.1.02,4]nonane bromide, monohydrate).

In another embodiment, the tiotropium salt in the pharmaceutical composition or pharmaceutical solution described herein is amorphous tiotropium bromide.

In another embodiment, the tiotropium salt in the pharmaceutical composition or pharmaceutical solution described herein is anhydrous tiotropium bromide.

In another embodiment, the tiotropium salt in the pharmaceutical composition or pharmaceutical solution described herein is anhydrous amorphous tiotropium bromide.

The pharmaceutical composition or solution may include from about 0.001 mg to about 0.3 mg of tiotropium or its salt (such as tiotropium bromide), such as from about 0.010 mg to about 0.280 mg; about 0.020 mg to about 0.260 mg; about 0.025 mg to about 0.240 mg; about 0.005 mg to about 0.1 mg; about 0.005 mg to about 0.05 mg; about 0.01 mg to about 0.04 mg; about 0.02 to about 0.07 mg; about 0.04 mg to about 0.08 mg; about 0.04 mg to about 0.10 mg; about 0.05 mg to about 0.15 mg; about 0.10 mg to about 0.19 mg; about 0.15 mg to about 0.20 mg; about 0.20 mg to about 0.25 mg; or from about 0.26 mg to about 0.30 mg tiotropium or its salt. The pharmaceutical composition or solution may include from about 0.001 mg to about 0.3 mg of tiotropium or its salt (such as tiotropium bromide), such as from about 0.010 mg to about 0.280 mg; about 0.020 mg to about 0.260 mg; about 0.025 mg to about 0.240 mg; about 0.005 mg to about 0.1 mg; about 0.005 mg to about 0.05 mg; about 0.01 mg to about 0.04 mg; about 0.02 to about 0.07 mg; about 0.04 mg to about 0.08 mg; about 0.04 mg to about 0.10 mg; about 0.05 mg to about 0.15 mg; about 0.10 mg to about 0.19 mg; about 0.15 mg to about 0.20 mg; about 0.20 mg to about 0.25 mg; or from about 0.26 mg to about 0.30 mg tiotropium per unit dosage of pharmaceutical composition or solution.

The pharmaceutical composition or solution may include from about 1 µg to about 100 µg of tiotropium or its salt (such as tiotropium bromide), such as from about 10 µg to about 80 µg, for example, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg of tiotropium or its salt. In one preferred embodiment, the volume of the pharmaceutical composition or solution is 2 mL.

One embodiment is a 2 mL pharmaceutical composition, such as a solution, containing about 80 µg tiotropium bromide. Another embodiment is a 2 mL pharmaceutical composition, such as a solution, containing about 75 µg tiotropium bromide. Yet another embodiment is a 2 mL pharmaceutical composition, such as a solution, containing about 70 µg tiotropium bromide. Yet another embodiment is a 2 mL pharmaceutical composition, such as a solution, containing about 65 µg tiotropium bromide. Yet another embodiment is a 2 mL pharmaceutical composition, such as a solution, containing about 60 µg tiotropium bromide. Yet another embodiment is a 2 mL pharmaceutical composition, such as a solution, containing about 55 µg tiotropium bromide. Yet another embodiment is a 2 mL pharmaceutical composition, such as a solution, containing about 50 µg tiotropium bromide. Yet another embodiment is a 2 mL pharmaceutical composition, such as a solution, containing about 45 µg tiotropium bromide. Yet another embodiment is a 2 mL pharmaceutical composition, such as a solution, containing about 40 µg tiotropium bromide. Yet another embodiment is a 2 mL pharmaceutical composition, such as a solution, containing about 35 µg tiotropium bromide. Yet another embodiment is a 2 mL pharmaceutical composition, such as a solution, containing about 30 µg tiotropium bromide. Yet another embodiment is a 2 mL pharmaceutical composition, such as a solution, containing about 25 µg tiotropium bromide. Yet another embodiment is a 2 mL pharmaceutical composition, such as a solution, containing about 20 µg tiotropium bromide. Yet another embodiment is a 2 mL pharmaceutical composition, such as a solution, containing about 15 µg tiotropium bromide. Yet another embodiment is a 2 mL pharmaceutical composition, such as a solution, containing about 10 µg tiotropium bromide. Yet another embodiment is a 2 mL pharmaceutical composition, such as a solution, containing about 5 µg tiotropium bromide.

The pharmaceutical composition or solution may include from about 0.0001% to about 0.030% by weight tiotropium or its salt (such as tiotropium bromide), such as from about 0.0002 wt % to about 0.02 wt %; about 0.0003 wt % to about 0.01 wt %; about 0.0005 wt % to about 0.008 wt %; about 0.0002 wt % to about 0.001 wt %; about 0.001 wt % to about 0.005 wt %; about 0.006 wt % to about 0.010 wt %; about 0.011 wt % to about 0.015 wt %; about 0.016 wt % to about 0.020 wt %; about 0.021 wt % to about 0.025 wt %; or from about 0.026 wt % to about 0.030 wt % tiotropium or its salt, based on 100% total weight of pharmaceutical composition or solution.

In additional embodiments, the complexing agent (such as disodium EDTA) is present in the pharmaceutical composition or solution at a concentration of less than about 0.1% by weight, such as less than about 0.09%, less than about 0.08%, less than about 0.07%, less than about 0.06%, less than about 0.05%, less than about 0.04%, less than about 0.03%, about 0.02%, or less than about 0.01% by weight.

In additional embodiments, the pharmaceutical composition or solution may contain about 0.01% complexing agent about 0.02% complexing agent, about 0.03% complexing agent, about 0.04% complexing agent, about 0.05% complexing agent, about 0.06% complexing agent, about 0.07% complexing agent, about 0.08% complexing agent about 0.09% complexing agent or about 0.1% complexing agent by weight.

In additional embodiments, the pharmaceutical composition or solution may contains about 0.01% disodium EDTA, about 0.02% disodium EDTA, about 0.03% disodium EDTA, about 0.04% disodium EDTA, about 0.05% disodium EDTA, about 0.06% disodium EDTA, about 0.07% disodium EDTA about 0.08% disodium EDTA about 0.09% disodium EDTA or about 0.1% disodium EDTA by weight. In one preferred embodiment, the pharmaceutical composition or solution contains about 0.01% disodium EDTA. In another preferred embodiment, the pharmaceutical composition or solution contains about 0.02% disodium EDTA. In yet another preferred embodiment, the pharmaceutical composition or solution contains about 0.05% disodium EDTA.

One embodiment is a pharmaceutical solution suitable for administration with a nebulizer consisting essentially of
 (a) about 0.0005% to about 0.008% w/w tiotropium or a pharmaceutically acceptable salt thereof,
 (b) about 0% to about 0.008% disodium EDTA;
 (c) about 0% to about 0.9% sodium chloride; and
 (d) water, based upon 100% total weight of the pharmaceutical solution, wherein the pH of the pharmaceutical composition is about 2 to about 4 (such as about 2.7). In one preferred embodiment, the pharmaceutical solution is free, or substantially free, of quaternary ammonium preservatives. In another preferred embodiment, the pharmaceutical solution is free, or substantially free, of preservatives.

In one embodiment, the pharmaceutical composition or solution provided herein has a long shelf life, i.e., it is stable during long term storage. The pharmaceutical composition or solution may contain greater than about 80%, such as greater than about 85%, greater than about 90%, greater than about 95% or greater than about 98% of the initial amount of tiotropium or its salt in the pharmaceutical composition or solution after being stored for 3 or 6 months or 1, 2 or 3 years at 25° C. when stored in a suitable low density polyethylene (LDPE) container.

Yet another embodiment is a container containing a pharmaceutical composition or solution of the present invention, wherein the volume of the composition or solution is from about 0.1 ml to about 5 ml, such as from about 1 ml to about 3 ml, or from about 1.5 ml to about 2.5 ml. In another embodiment, the volume of the tiotropium solution of the present invention is from about 0.05 ml to about 1.0 ml; such as from about 0.1 ml to about 0.9 ml; from about 0.1 ml to about 0.8 ml; from about 0.1 ml to about 0.7 ml; from about 0.1 ml to about 0.6 ml; from about 0.1 ml to about 0.5 ml; from about 0.1 ml to about 0.4 ml; from about 0.1 ml to about 0.3 ml; or from about 0.1 ml to about 0.2 ml.

The pharmaceutical composition or solution may have a pH of between about 2.0 and about 6.0. For example, the pharmaceutical composition or solution may have a pH of from about 2.0 to about 4.0. The preferred pH range of tiotropium bromide solutions is from about 2.0 to about 4.5, preferably from about 2.5 to 3.5, most preferably from about 2.7 to about 3.2. In one embodiment, the pharmaceutical composition or solution has a pH of about 2.5, about 2.6, about 2.7, about 2.8, about 2.9, about 3.0, about 3.1, about 3.2, about 3.3, about 3.4, or about 3.5.

In another embodiment of the present invention, the inhalation solution has a pH from about 2.2 to about 2.9.

The osmolality of the pharmaceutical composition or solution may be from about 200 to about 500 mOsm/kg. In other embodiments of the present invention, the osmolality of the solution may be between about 275 and about 325 mOsm/kg.

In another embodiment, the pharmaceutical composition of the present invention comprises about 0.002% to about 0.01% w/w tiotropium or any pharmaceutically acceptable salt thereof, about 0% to about 0.01% w/w EDTA, about 0.9% sodium chloride, wherein the composition is free of preservative and wherein the composition has a pH in the range of about 2.0 to about 4.0.

Another embodiment is a prepackaged, sterile, premixed, premeasured tiotropium bromide inhalation solution. Preferably, the solution is a ready-to-use solution which does not require any mixing or dilution by the subject prior to administration. The solution may be administered for the relief of bronchospasm in a subject suffering from COPD.

Yet another embodiment is one or more prefilled containers containing a pharmaceutical composition or solution of the present invention. In one embodiment, each container comprises a single unit dose of a pharmaceutical composition or solution of the present invention comprising a therapeutically effective amount of tiotropium or its salt for the treatment of COPD. In one embodiment, each container includes a sterile, premixed, premeasured, substantially benzalkonium chloride free inhalation solution comprising a single unit dose of a therapeutically effective amount of tiotropium or its salt in a single container.

One embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.01% by weight of disodium EDTA, wherein the composition is free of preservative, and the composition has a pH of from about 2.5 to about 3.5. The sodium chloride may be present at about 0.9% by weight. In one embodiment, the pH of the pharmaceutical composition is about 2.7. In another embodiment, the pH of the pharmaceutical composition is about 2.8. In yet another embodiment, the pH of the pharmaceutical composition is about 2.9. In yet another embodiment, the pH of the pharmaceutical composition is about 3.0.

Another embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.02% by weight of disodium EDTA, wherein the composition is free of preservative, and the composition has a pH of from about 2.5 to about 3.5.

Yet another embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.05% by weight of disodium EDTA, wherein the composition is free of preservative, and the composition has a pH of from about 2.5 to about 3.5.

Yet another embodiment is a method of administering tiotropium or a salt thereof comprising administering by inhalation to a subject a pharmaceutical composition or solution of the present invention.

Yet another embodiment is a method of relieving bronchospasm (such as that associated with COPD) comprising administering by inhalation to a subject in need thereof a pharmaceutical composition or solution of the present invention.

Yet another embodiment is a kit and/or system for administering a bronchodilator to relieve bronchospasm, for instance, bronchospasm associated with COPD. The kit and/or system may comprise a pharmaceutical composition or solution of the present invention. In one embodiment, the kit and/or system comprises an inhalation solution of the present invention comprising a therapeutically effective amount of tiotropium in a prepackaged, premeasured, premixed and/or single unit dose form for the treatment of COPD. In another embodiment, the prepackaged inhalation kit and/or system comprises one or more premixed, premeasured single unit dose vials comprising a pharmaceutical composition or solution of the present invention containing a therapeutically effective amount of tiotropium for the treatment of bronchospasm (such as that associated with COPD), and instructions for using the same.

Yet another embodiment is a kit comprising a nebulizer, instructions for using the nebulizer and the unit dose vials containing the pharmaceutical compositions of the present invention.

Yet another embodiment is a kit for the treatment, prevention or amelioration or one or more symptoms of diseases or disorders associated with bronchoconstriction which comprises:
(i) a nebulizer;
(ii) a nebulizable composition for the treatment, prevention or amelioration or one or more symptoms of diseases or disorders associated with bronchoconstriction (such a pharmaceutical composition or solution of the present invention) which comprises:
(a) tiotropium or its salt; and
(b) water.

A further embodiment of the present invention is to provide a process for making an inhalation solution comprising tiotropium for use in relieving bronchospasm associated with COPD. In one embodiment, the process comprises the steps of:
(a) dissolving tiotropium or its salt in water;
(b) optionally addition of pharmaceutically acceptable excipients such as a buffer, complexing agent, tonicity adjusting agent, or any combination thereof, to the solution of step (a);
(c) optionally adjusting the pH of the solution (for example, the solution of step (a) or step (b)) with a pharmaceutically acceptable acid;
(d) optionally filtering the solution (for example, with a 0.2 micron filter); and
(e) filling a suitable container with the solution.

In another embodiment, the process comprises the steps of:
(a) dissolving tiotropium or its salt in water;
(b) optionally addition of pharmaceutically acceptable excipients such as a buffer, complexing agent, tonicity adjusting agent, or any combination thereof, to the solution of step (a);
(c) optionally adjusting the pH of the solution (for example, the solution of step (a) or step (b)) with a pharmaceutically acceptable acid;
(d) filtering the solution (for example, with a 0.2 micron filter); and
(e) filling a suitable container with the solution.

Yet another embodiment is a method of preparing a pharmaceutical composition comprising about 0.0001% to about 0.03% by weight of tiotropium or a pharmaceutically acceptable salt thereof, water, about 0.01% to about 0.1% by weight of a complexing agent, and about 0% to about 0.9% by weight of sodium chloride, wherein the composition has a pH ranging from about 2.5 to about 3.5 and is free of preservative. The process includes the steps of:
(a) dissolving sodium chloride in water to form a solution;
(b) adding a complexing agent to the solution of step (a);
(c) adjusting the pH of the solution of step (b) (for example, by adding hydrochloric acid) to about 2.5 to about 3.5;
(d) adding tiotropium or a pharmaceutically acceptable salt thereof;
(e) filtering the solution of step (d); and
(f) filling a container with the solution of step (e).

Another embodiment of the invention relates to a device comprising tiotropium or a salt thereof, for example, for use in relieving the symptoms of COPD.

Yet another embodiment is a method for improving user compliance and/or quality of life as compared to conventional treatments for COPD. The method comprises initiating treatment with the pharmaceutical composition or solution of the present invention, or a container, kit, or system of the present invention. The present invention provides convenient, fast and reliable treatment for COPD that represents an improvement over traditional COPD treatments.

Other objects, features and advantages of the present invention will be apparent to those of ordinary skill in the art in view of the following detailed description of the invention and accompanying drawings.

DETAILED DESCRIPTION OF THE INVENTION

Salts of tiotropium include, but are not limited to, acid addition salts and base salts thereof, solvates thereof, and any mixture thereof. Suitable salts of tiotropium include, but are not limited to, halide salts such as bromide, chloride and iodide salts. These and other salts are described, for example, in U.S. Pat. No. RE 39,820, which is hereby incorporated by reference in its entirety. The preparation of the tiotropium bromide monohydrate is described in U.S. Pat. No. 6,777,423, which is incorporated herein by reference in its entirety. Tiotropium and its salts can be administered to provide a bronchodilation effect and relief from symptoms associated with COPD.

Tiotropium bromide has a molecular weight of 472.416 g/mol and the empirical formula $C_{19}H_{22}BrNO_4S_2$. Tiotropium bromide monohydrate is sparingly soluble in water and soluble in methanol. The established chemical structure of tiotropium bromide monohydrate is as follows:

The term "tiotropium" as used herein, include acids, salts, esters, hydrates, polymorphs, hemihydrates, solvates, and derivatives thereof.

2-hydroxy-2,2-dithiophen-2-ylacetic acid is an impurity of Tiotropium identified as Impurity A in the present invention.

In the present invention, tiotropium may be provided in a variety of pharmaceutically acceptable vehicles, including, but not limited to, water or hydroalcoholic solution or any other aqueous solution comprising a pharmaceutically acceptable amount of an osmotic agent.

In a preferred embodiment, the tiotropium salt in the pharmaceutical composition or pharmaceutical solution described herein is tiotropium bromide, such as tiotropium bromide monohydrate ((1α,2β,4β,7β)-7-[hydroxydi-2-thienylacetyl)oxy]-9,9-dimethyl-3-oxa-9-azoniatricyclo [3.3.1.02,4]nonane bromide, monohydrate).

In another embodiment, the tiotropium salt in the pharmaceutical composition or pharmaceutical solution described herein is amorphous tiotropium bromide.

In another embodiment, the tiotropium salt in the pharmaceutical composition or pharmaceutical solution described herein is anhydrous tiotropium bromide.

In another embodiment, the tiotropium salt in the pharmaceutical composition or pharmaceutical solution described herein is anhydrous amorphous tiotropium bromide.

To treat indications with a therapeutic agent, an "effective amount" of a therapeutic agent will be recognized by clinicians and persons of ordinary skill in the art, and includes an amount effective to treat, reduce, alleviate, ameliorate, eliminate or prevent one or more symptoms of the condition sought to be treated, or alternately, the condition sought to be avoided, or to otherwise produce a clinically recognizable favorable change in the condition or its effects.

In another embodiment, the present invention provides sterile pharmaceutical composition of tiotropium for inhalation wherein the composition is substantially free of preservative, preferably substantially benzalkonium chloride free to treat bronchospasm associated with COPD.

A composition is "substantially benzalkonium chloride free" or "substantially free of benzalkonium chloride" when the amount of benzalkonium chloride is not an amount sufficient to materially act as a preservative for the pharmaceutical composition or solution. Moreover, in a "substantially benzalkonium chloride free" or "substantially free of benzalkonium chloride" composition, benzalkonium chloride may be present in concentration less than 0.008% w/w based on total weight of composition or solution. The term "substantially free of preservative" denotes that preservative may be present in concentration less than 0.008% w/w based on total weight of composition or solution.

Generally, pharmaceutical inhalation solutions contain a preservative such as benzalkonium chloride. One problem with these solutions is that the benzalkonium chloride may cause paradoxic bronchoconstriction if the solution is administered repeatedly over short intervals and frequent exposure to benzalkonium chloride may lead to occupational asthma. Another problem is that, when inhaled by patients, the benzalkonium chloride can cause dose-dependent bronchoconstriction. The inhalation solutions of the present invention may be provided without benzalkonium chloride, thereby making them suitable, especially in situations where the inhalation solution is administered repeatedly over a short period of time. Also, administering a substantially benzalkonium chloride-free inhalation solution to a patient reduces the concomitant liability of adverse effects associated with benzalkonium chloride alone or in combination other excipients and/or tiotropium. It also negates the toxicity and other side effects associated with benzalkonium chloride.

The inhalation solutions of the present invention may also be provided in sterile, unit dose treatments.

In another embodiment of the present invention, there is provided a sterile, unit dose pharmaceutical solution composition for inhalation via nebulization comprising tiotropium or its salt wherein the composition is substantially free of a complexing agent such as ethylene diamine tetra-acetic acid (EDTA).

One embodiment is a pharmaceutical composition comprising
(i) tiotropium or its pharmaceutically acceptable salts thereof
(ii) water
wherein said composition is free of preservative and complexing agent.

Low pH levels, particularly below 3.2, are preferred for the long-term stability of the tiotropium salts in the formulation. The absence of or reduction in the concentration of the additive EDTA also helps to reduce the paradoxic effect associated with cough.

In another embodiment of the present invention, the inhalation solution has a pH of from about 2.0 to about 6.0. In another embodiment, the solution has a pH of from about 2.0 to about 4.0. The preferred pH range of tiotropium bromide solutions is from about 2.0 to about 4.5, preferably from about 2.5 to 3.5, most preferably from about 2.7 to about 3.2. In one embodiment, the pharmaceutical composition or solution has a pH of about 2.5, about 2.6, about 2.7, about 2.8, about 2.9, about 3.0, about 3.1, about 3.2, about 3.3, about 3.4, or about 3.5.

In another embodiment of the present invention, the inhalation solution has a pH from about 2.2 to about 2.9.

The pH may be adjusted by the addition of one or more pharmaceutically acceptable acids. Examples of suitable pharmaceutically acceptable acids include inorganic acids, such as hydrochloric acid, hydrobromic acid, nitric acid, sulfuric acid, and phosphoric acid, and combinations thereof. Examples of other suitable pharmacologically acceptable acids include organic acids, such as ascorbic acid, citric acid, malic acid, maleic acid, tartaric acid, succinic acid, fumaric acid, acetic acid, formic acid, and/or propionic acid. In one embodiment, the pH is adjusted with 1N hydrochloric acid or 1N sulfuric acid. In another embodiment, the pH is adjusted with one or more organic acids selected from ascorbic acid, fumaric acid and citric acid. A preferred organic acid is citric acid. If desired, mixtures of the abovementioned acids may also be used, particularly in the case of acids which have other properties in addition to their acidifying properties, e.g., those which act as flavorings or antioxidants, such as for example citric acid or ascorbic acid.

The inhalation solution of the present invention may contain sodium citrate at a concentration of about 0.1 to about 1.0% (w/w) and citric acid at a concentration of about 0.1 to 1.0% (w/w) to control pH.

The inhalation solution may optionally include a buffer. General and biological buffers in the pH range of about 2.0 to about 8.0 include, but are not limited to, acetate, barbital, borate, Britton-Robinson, cacodylate, citrate, collidine, formate, maleate, McIlvaine, phosphate, Prideaux-Ward, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, and AMPD buffers.

In another embodiment of the present invention, a therapeutically effective amount of tiotropium may include from about 0.001 mg to about 0.3 mg of tiotropium bromide. Therapeutically effective amounts may also include the following intermediate ranges of tiotropium bromide: from about 0.010 mg to about 0.280 mg; about 0.020 mg to about 0.260 mg; about 0.025 mg to about 0.240 mg; about 0.005 mg to about 0.1 mg; about 0.005 mg to about 0.05 mg; about 0.01 mg to about 0.04 mg; about 0.02 to about 0.07 mg; about 0.04 mg to about 0.08 mg; about 0.04 mg to about 0.10 mg; about 0.05 mg to about 0.15 mg; about 0.10 mg to about 0.19 mg; about 0.15 mg to about 0.20 mg; 0.20 mg to about 0.25 mg; and about 0.26 mg to about 0.30 mg. The pharmaceutical composition or solution may include from about 0.001 mg to about 0.3 mg of tiotropium or its salt (such as tiotropium bromide), such as from about 0.010 mg to about 0.280 mg; about 0.020 mg to about 0.260 mg; about 0.025 mg to about 0.240 mg; about 0.005 mg to about 0.1 mg;

about 0.005 mg to about 0.05 mg; about 0.01 mg to about 0.04 mg; about 0.02 to about 0.07 mg; about 0.04 mg to about 0.08 mg; about 0.04 mg to about 0.10 mg; about 0.05 mg to about 0.15 mg; about 0.10 mg to about 0.19 mg; about 0.15 mg to about 0.20 mg; about 0.20 mg to about 0.25 mg; or from about 0.26 mg to about 0.30 mg tiotropium per unit dosage of pharmaceutical composition or solution.

The pharmaceutical composition or solution may include from about 1 µg to about 100 µg of tiotropium or its salt (such as tiotropium bromide), such as from about 10 µg to about 80 µg, for example, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg of tiotropium or its salt. In one preferred embodiment, the volume of the pharmaceutical composition or solution is 2 mL.

One embodiment is a 2 mL pharmaceutical composition, such as a solution, containing about 80 µg tiotropium bromide. Another embodiment is a 2 mL pharmaceutical composition, such as a solution, containing about 75 µg tiotropium bromide. Yet another embodiment is a 2 mL pharmaceutical composition, such as a solution, containing about 70 µg tiotropium bromide. Yet another embodiment is a 2 mL pharmaceutical composition, such as a solution, containing about 65 µg tiotropium bromide. Yet another embodiment is a 2 mL pharmaceutical composition, such as a solution, containing about 60 µg tiotropium bromide. Yet another embodiment is a 2 mL pharmaceutical composition, such as a solution, containing about 55 µg tiotropium bromide. Yet another embodiment is a 2 mL pharmaceutical composition, such as a solution, containing about 50 µg tiotropium bromide. Yet another embodiment is a 2 mL pharmaceutical composition, such as a solution, containing about 45 µg tiotropium bromide. Yet another embodiment is a 2 mL pharmaceutical composition, such as a solution, containing about 40 µg tiotropium bromide. Yet another embodiment is a 2 mL pharmaceutical composition, such as a solution, containing about 35 µg tiotropium bromide. Yet another embodiment is a 2 mL pharmaceutical composition, such as a solution, containing about 30 µg tiotropium bromide. Yet another embodiment is a 2 mL pharmaceutical composition, such as a solution, containing about 25 µg tiotropium bromide. Yet another embodiment is a 2 mL pharmaceutical composition, such as a solution, containing about 20 µg tiotropium bromide. Yet another embodiment is a 2 mL pharmaceutical composition, such as a solution, containing about 15 µg tiotropium bromide. Yet another embodiment is a 2 mL pharmaceutical composition, such as a solution, containing about 10 µg tiotropium bromide. Yet another embodiment is a 2 mL pharmaceutical composition, such as a solution, containing about 5 µg tiotropium bromide.

In another embodiment of the present invention, a therapeutically effective amount of tiotropium may include from about 0.0001% to about 0.030% by weight tiotropium bromide, including the following intermediate ranges of tiotropium bromide: about 0.0002 wt % to about 0.02 wt %; about 0.0003 wt % to about 0.01 wt %; about 0.0005 wt % to about 0.008 wt %; about 0.0002 wt % to about 0.001 wt %; about 0.001 wt % to about 0.005 wt %; about 0.006 wt % to about 0.010 wt %; about 0.011 wt % to about 0.015 wt %; about 0.016 wt % to about 0.020 wt %; about 0.021 wt % to about 0.025 wt %; or about 0.026 wt % to about 0.030 wt %.

In additional embodiments, the complexing agent (such as disodium EDTA) is present in the pharmaceutical composition or solution at a concentration of less than about 0.1% by weight, such as less than about 0.09%, less than about 0.08%, less than about 0.07%, less than about 0.06%, less than about 0.05%, less than about 0.04%, less than about 0.03%, about 0.02%, or less than about 0.01% by weight.

In additional embodiments, the pharmaceutical composition or solution may contain about 0.01% complexing agent about 0.02% complexing agent, about 0.03% complexing agent, about 0.04% complexing agent, about 0.05% complexing agent, about 0.06% complexing agent, about 0.07% complexing agent, about 0.08% complexing agent about 0.09% complexing agent or about 0.1% complexing agent by weight.

In additional embodiments, the pharmaceutical composition or solution may contains about 0.01% disodium EDTA, about 0.02% disodium EDTA, about 0.03% disodium EDTA, about 0.04% disodium EDTA, about 0.05% disodium EDTA, about 0.06% disodium EDTA, about 0.07% disodium EDTA about 0.08% disodium EDTA about 0.09% disodium EDTA or about 0.1% disodium EDTA by weight. In one preferred embodiment, the pharmaceutical composition or solution contains about 0.01% disodium EDTA. In another preferred embodiment, the pharmaceutical composition or solution contains about 0.02% disodium EDTA. In yet another preferred embodiment, the pharmaceutical composition or solution contains about 0.05% disodium EDTA.

One embodiment is a pharmaceutical solution suitable for administration with a nebulizer consisting essentially of
  (a) about 0.0005% to about 0.008% w/w tiotropium or a pharmaceutically acceptable salt thereof,
  (b) about 0% to about 0.008% disodium EDTA;
  (c) about 0% to about 0.9% sodium chloride; and
  (d) water,
based upon 100% total weight of the pharmaceutical solution, wherein the pH of the pharmaceutical composition is about 2 to about 4 (such as about 2.7). In one preferred embodiment, the pharmaceutical solution is free, or substantially free, of quaternary ammonium preservatives. In another preferred embodiment, the pharmaceutical solution is free, or substantially free, of preservatives.

In one embodiment, the pharmaceutical composition or solution provided herein has a long shelf life, i.e., it is stable during long term storage. The pharmaceutical composition or solution may contain greater than about 80%, such as greater than about 85%, greater than about 90%, greater than about 95% or greater than about 98% of the initial amount of tiotropium or its salt in the pharmaceutical composition or solution after being stored for 3 or 6 months or 1, 2 or 3 years at 25° C. when stored in a suitable LDPE container, cyclic olefin polymer container, cyclic olefin copolymer container, or glass container. The stability may be determined using Arrhenius kinetics.

Another embodiment is a container containing a pharmaceutical composition or solution of the present invention, wherein the volume of the composition or solution is from about 0.1 ml to about 5 ml, such as from about 1 ml to about 3 ml, or from about 1.5 ml to about 2.5 ml. In another embodiment, the volume of the tiotropium solution of the present invention is from about 0.05 ml to about 1.0 ml; such as from about 0.1 ml to about 0.9 ml; from about 0.1 ml to about 0.8 ml; from about 0.1 ml to about 0.7 ml; from about 0.1 ml to about 0.6 ml; from about 0.1 ml to about 0.5 ml; from about 0.1 ml to about 0.4 ml; from about 0.1 ml to about 0.3 ml; or from about 0.1 ml to about 0.2 ml.

In another embodiment, the pharmaceutical composition of the present invention comprises about 0.002% to about 0.01% w/w tiotropium or any pharmaceutically acceptable salt thereof, about 0% to about 0.01% w/w EDTA, about 0.9% sodium chloride, wherein the composition is free of preservative and wherein the composition has a pH in the range of about 2.0 to about 4.0.

Another embodiment is a prepackaged, sterile, premixed, premeasured tiotropium inhalation solution for the relief of bronchospasm in patients suffering from COPD.

Another embodiment of the present invention is to provide a substantially benzalkonium chloride free tiotropium inhalation solution to treat bronchospasm associated with COPD. In another embodiment, the present invention comprises one or more prefilled containers. Each container comprises a single unit dose of an aqueous solution comprising a therapeutically effective amount of tiotropium for the treatment of COPD. In another embodiment, the present invention relates to a sterile, premixed, premeasured, substantially benzalkonium chloride free inhalation solution comprising a single unit dose of a therapeutically effective amount of tiotropium in a single container.

One embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.01% by weight of disodium EDTA, wherein the composition is free of preservative, and the composition has a pH of from about 2.5 to about 3.5. The sodium chloride may be present at about 0.9% by weight. In one embodiment, the pH of the pharmaceutical composition is about 2.7. In another embodiment, the pH of the pharmaceutical composition is about 2.8. In yet another embodiment, the pH of the pharmaceutical composition is about 2.9. In yet another embodiment, the pH of the pharmaceutical composition is about 3.0.

Another embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.02% by weight of disodium EDTA, wherein the composition is free of preservative, and the composition has a pH of from about 2.5 to about 3.5.

Yet another embodiment is a prefilled container containing about 2 mL of an aqueous pharmaceutical composition consisting of (i) from about 10 to about 80 µg of tiotropium bromide, (ii) sodium chloride, (iii) hydrochloric acid (e.g., in an amount sufficient to adjust the pH of the pharmaceutical composition, such as to about 2.5 to about 3.5), and (iv) about 0.05% by weight of disodium EDTA, wherein the composition is free of preservative, and the composition has a pH of from about 2.5 to about 3.5.

A further embodiment of the present invention is to provide a method for treating or relieving bronchospasm associated with COPD comprising administering to a patient in need thereof a tiotropium inhalation formulation according to any of the embodiments described herein.

An additional embodiment of the present invention is to provide a kit and/or system for administering a bronchodilator to relieve bronchospasm associated with COPD. In an alternative embodiment, the kit and/or system of the present invention comprises an inhalation solution comprising a therapeutically effective amount of tiotropium in a prepackaged, premeasured, premixed and/or single unit dose form for the treatment of COPD. In another alternative embodiment, the prepackaged inhalation kit and/or system of the present invention provides one or more premixed, premeasured single unit dose vials comprising a therapeutically effective amount of tiotropium for the treatment of bronchospasm associated with COPD, and instructions for using the same.

More specifically, the present invention provides a kit for the treatment, prevention or amelioration or one or more symptoms of diseases or disorders associated with broncho constriction which comprises:

(i) a nebulizer;
(ii) a nebulizable composition for the treatment, prevention or amelioration or one or more symptoms of diseases or disorders associated with bronchoconstriction which comprises:
   (a) tiotropium or a salt thereof; and
   (b) water.

Yet another embodiment is a kit comprising a nebulizer, instructions for using the nebulizer and the unit dose vials containing the pharmaceutical compositions of the present invention.

In another embodiment of the present invention, the osmolality of the inhalation solution may be from about 200 to about 500 mOsm/kg. In another embodiment, the osmolality of the solution may be from about 275 to about 325 mOsm/kg. In a further embodiment, the compositions of the present invention may comprise about 0.4 to about 1.0 weight percent ionic salt.

Suitable tonicity adjusting agents may include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethyl sulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine, zinc sulfate, and mixtures thereof.

Suitable osmotic adjusting agents that may be used include, but are not limited to, sodium chloride, potassium chloride, zinc chloride, calcium chloride and mixtures thereof. Other osmotic adjusting agents may also include, but are not limited to, mannitol, glycerol, dextrose and mixtures thereof.

Any cosolvent that is suitable for inhalation and capable of dissolving or solubilizing the tiotropium in the mixture of cosolvent and water can be used. Examples of suitable cosolvents include, for example, alcohols, ethers, hydrocarbons, and perfluorocarbons. Preferably, the cosolvent is a short chain polar alcohol. More preferably, the cosolvent is an aliphatic alcohol having from one to six carbon atoms, such as ethanol or isopropanol. The most preferred cosolvent is ethanol. Examples of suitable hydrocarbons include n-butane, isobutane, pentane, neopentane and isopentanes. Examples of suitable ethers include dimethyl ether and diethyl ether. Examples of suitable perfluorocarbons include perfluoropropane, perfluorobutane, perfluorocyclobutane, and perfluoropentane.

When ethanol is utilized as the cosolvent, the cosolvent is usually present in an amount of from about 1% to about 40% by weight, based on the total weight of the formulation. The ethanol should be present in an amount which fully dissolves or solubilizes tiotropium in the mixture of ethanol and water. Preferably, ethanol is present in amount sufficient to fully maintain the tiotropium in solution at freezing temperatures, such as 0° C. In general, as the temperature is decreased, the solubility of active ingredient in ethanol is decreased. Therefore, an excess of ethanol over the amount required to fully dissolve or solubilize active ingredient at ambient or room temperature is preferred. In this regard, ethanol is preferably present in an amount of at least 10% by weight, more preferably at least 15% by weight, even more preferably at least 20% by weight, and most preferably at least 25% by weight. Based on the disclosure provided herein, one skilled in the art will recognize that lower concentrations of active ingredient usually require lower concentrations of cosolvent, and vice versa, in order to form a stable solution.

Suitable surfactants that may be used include, but are not limited to, C5-20-fatty alcohols, C5-20-fatty acids, C5-20-fatty acid esters, lecithin, glycerides, propyleneglycol esters, polyoxyethylenes, polysorbates, sorbitan esters and/or carbohydrates. C5-20-fatty acids, propyleneglycol diesters and/or triglycerides and/or sorbitans of the C5-20-fatty acids are preferred, while oleic acid and sorbitan mono-, di- or trioleates are particularly preferred.

Suitable antioxidants that may be used include, but are not limited to, ascorbic acid, for example, provided that it has not already been used to adjust the pH, vitamin A, vitamin E, tocopherols and similar vitamins or pro-vitamins occurring in the human body.

The inhalation solution may be contained in a unit-dose, low-density polyethylene (LDPE) container, polypropylene container, or a cyclic polyolefin container. Each unit-dose container may be disposed in a foil pouch, and each foil pouch may contain 2 or more unit-dose containers. Each foil pouch containing the unit dose container may be disposed in a shelf carton. The inhalation solution comprises a single unit dose of a therapeutically effective amount of tiotropium. Such system and/or kit may provide such containers in prepackaged form. The container with a TWIST-FLEX™ top prefer, such top comprising an easy-to-grip tab-like handle such that the container may be opened, for example, by twisting off the tab by hand. The TWIST-FLEX™ top is advantageous in that it allows for easy dispensing of the solution, prevents spillage and eliminates the need to open the container or tearing by cutting or tearing off the top, or the like, thereby reducing cross-contamination. One or more of the semi-permeable single unit dose containers may be prepackaged in aluminum foil pouch, such that the foil provides a protective barrier against environmental contaminants and light as it helps to improves the shelf-life and stability of the inhalation solution. Dispensing vials may include, but are not limited to, any container comprising glass, low density polyethylene, polypropylene, cyclic polyolefins or any other material capable of preventing the solution from leaking out of the container. The vial may be enclosed by any conventional means including, but not limited to, screw cap, heat seal, snap-on top, flip-top, twist-off stopper, peel away top, and the like.

The inhalation solution of the present invention may be administered by nebulizer. Suitable nebulizers include, but are not limited to, a jet nebulizer, an ultrasonic nebulizer, vibrating mesh nebulizer and a breath actuated nebulizer. Preferably, the nebulizer is a jet nebulizer connected to an air compressor with adequate airflow. The nebulizer being equipped with a mouthpiece or suitable face mask. The inhalation solution may be administered by nebulizers manufactured, designed or sold by Omron, such as the Omron MICRO AIR™ Ultrasonic Nebulizer. Other nebulizers may also include those manufactured, designed, or sold by Aerogen. Additionally, the formulations described herein can also be nebulized using inhalers other than those described above, for example jet-stream inhalers.

Yet another embodiment is a method of preparing a pharmaceutical composition comprising about 0.0001% to about 0.03% by weight of tiotropium or a pharmaceutically acceptable salt thereof, water, about 0.01% to about 0.1% by weight of a complexing agent, and about 0% to about 0.9% by weight of sodium chloride, wherein the composition has a pH ranging from about 2.5 to about 3.5 and is free of preservative. The process includes the steps of:
(a) dissolving sodium chloride in water to form a solution;
(b) adding a complexing agent to the solution of step (a);
(c) adjusting the pH of the solution of step (b) (for example, by adding hydrochloric acid) to about 2.5 to about 3.5;
(d) adding tiotropium or a pharmaceutically acceptable salt thereof;
(e) filtering the solution of step (d); and
(f) filling a container with the solution of step (e).

The following non-limiting examples suitably illustrate the pharmaceutical compositions of the present invention.

Example 1

The pharmaceutical compositions of the invention may include the following ingredients in amounts as provided in the following table:

| Sr. No. | Ingredients | Range (% w/w) |
| --- | --- | --- |
| 1 | Tiotropium Bromide | 0.0005 to 0.1 |
| 2 | Benzalkonium Chloride | 0 to 0.008 |
| 3 | Di Sodium EDTA | 0.001 to 0.008 |
| 4 | Sodium Chloride | 0 to 0.9 |
| 5 | 1N HCl | 0 to 1.4 |
| 6 | Water for injection | q.s. |

Example 2

The pharmaceutical compositions of the invention may include following ingredients and amounts:

| Sr. No. | Ingredients | Range (% w/w) |
| --- | --- | --- |
| 1 | Tiotropium Bromide | 0.0005 to 0.1 |
| 2 | Citric acid | 0 to 0.008 |
| 3 | Sodium citrate | 0.001 to 0.008 |
| 4 | Sodium Chloride | 0 to 0.9 |
| 5 | 1N HCl | 0 to 1.4 |
| 6 | Water for injection | q.s. |

The pharmaceutical compositions from Example 1 and Example 2 may be sterilized by filtration (through a 0.2 micron filter) and filled into a suitable container. The solution compositions may be inserted into a suitable nebulizer and the patient breathes into the nebulizer to deliver the dosage into the lungs.

Example 3A

The pharmaceutical compositions of the invention may include the following:

| Sr. No | Ingredients | 10 mcg/ 2 ml | 20 mcg/ 2 ml | 40 mcg/ 2 ml | 80 mcg/ 2 ml |
|---|---|---|---|---|---|
| | | Quantity (% w/w) | | | |
| 1 | Tiotropium bromide anhydrous eq. to Tiotropium | 0.0005 | 0.001 | 0.002 | 0.004 |
| 2 | Sodium chloride | 0.9 | | | |
| 3 | Disodium edetate | 0.001 | | | |
| 4 | Hydrochloric acid as 1N HCl solution | q. s. to pH 2.7 | | | |
| 5 | Water for injection | q. s. | | | |

Manufacturing Process:

1. Collect 95% of batch quantity water for injection in manufacturing vessel. Cool water for injection to 15-25° C.
2. Add and dissolve to it batch quantity of sodium chloride under stirring. Check clarity of the solution.
3. Add and dissolve to it batch quantity of disodium edetate under stirring. Check clarity of the solution.
4. Check pH and adjust pH to 2.7 using 1N HCl solution.
5. Add and dissolve to it batch quantity of tiotropium bromide anhydrous under stirring. Check clarity of the solution.
6. Make up volume of bulk.
7. Filter bulk through 0.22μ PVDF filter.
8. Fill in suitable containers.

Example 3B

The pharmaceutical compositions in the table below may be prepared as described in Example 3A.

| Sr. No | Ingredients | 10 mcg/ 2 ml | 20 mcg/ 2 ml | 40 mcg/ 2 ml | 80 mcg/ 2 ml |
|---|---|---|---|---|---|
| | | Quantity (% w/w) | | | |
| 1 | Tiotropium bromide anhydrous eq. to Tiotropium | 0.0005 | 0.001 | 0.002 | 0.004 |
| 2 | Sodium chloride | 0.9 | | | |
| 3 | Disodium edetate | 0.01 | | | |
| 4 | Hydrochloric acid as 1N HCl solution | q. s. to pH 2.7 | | | |
| 5 | Water for injection | q. s. | | | |

The pharmaceutical compositions in the table above may also be prepared as with the pH adjusted to 2.8, 2.9, or 3.0.

Example 3C

The pharmaceutical compositions in the table below may be prepared as described in Example 3A.

| Sr. No | Ingredients | 10 mcg/ 2 ml | 20 mcg/ 2 ml | 40 mcg/ 2 ml | 80 mcg/ 2 ml |
|---|---|---|---|---|---|
| | | Quantity (% w/w) | | | |
| 1 | Tiotropium bromide anhydrous eq. to Tiotropium | 0.0005 | 0.001 | 0.002 | 0.004 |
| 2 | Sodium chloride | 0.9 | | | |
| 3 | Disodium edetate | 0.02 | | | |
| 4 | Hydrochloric acid as 1N HCl solution | q. s. to pH 2.7 | | | |
| 5 | Water for injection | q. s. | | | |

The pharmaceutical compositions in the table above may also be prepared as with the pH adjusted to 2.8, 2.9, or 3.0.

Example 3D

The pharmaceutical compositions in the table below may be prepared as described in Example 3A.

| Sr. No | Ingredients | 10 mcg/ 2 ml | 20 mcg/ 2 ml | 40 mcg/ 2 ml | 80 mcg/ 2 ml |
|---|---|---|---|---|---|
| | | Quantity (% w/w) | | | |
| 1 | Tiotropium bromide anhydrous eq. to Tiotropium | 0.0005 | 0.001 | 0.002 | 0.004 |
| 2 | Sodium chloride | 0.9 | | | |
| 3 | Disodium edetate | 0.05 | | | |
| 4 | Hydrochloric acid as 1N HCl solution | q. s. to pH 2.7 | | | |
| 5 | Water for injection | q. s. | | | |

The pharmaceutical compositions in the table above may also be prepared as with the pH adjusted to 2.8, 2.9, or 3.0.

Example 4

The below example illustrates the effect of different concentrations of EDTA on the stability of the composition

| | | 4A | | 4B | | 4C | |
|---|---|---|---|---|---|---|---|
| # | Ingredients | mcg/ 2 ml | % w/w | mcg/ 2 ml | % w/w | mcg/ 2 ml | % w/w |
| 1 | Tiotropium Bromide anhydrous eq. to tiotropium | 80 | 0.004 | 80 | 0.004 | 80 | 0.004 |
| 2 | Disodium EDTA | — | — | 20 | 0.001 | 200 | 0.01 |
| 3 | Sodium chloride | 18000 | 0.9 | 18000 | 0.9 | 18000 | 0.9 |
| 5 | 1N HCl solution | | | q.s. to pH 2.7 | | | |
| 6 | Water for injection | qs | qs | qs | qs | qs | qs |
| | pH of solution | 2.69 | | 2.71 | | 2.7 | |

| Stability data | | | |
|---|---|---|---|
| # | 4A | 4B | 4C |
| Related substances Impurity A (2-hydroxy-2,2-dithiophen-2-ylacetic acid) | | | |
| Initial | 0.02 | ND | 0.01 |
| 1 M 2-8° C. | 0.01 | 0.03 | 0.02 |
| 1M_25° C./60% RH | 0.05 | 0.06 | 0.05 |
| 1M_40° C./75% RH | 0.17 | 0.16 | 0.2 |
| Total impurities | | | |
| Initial | 0.07 | ND | 0.06 |
| 1 M 2-8° C. | 0.08 | 0.00 | 0.12 |
| 1M_25° C./60% RH | 0.13 | 0.09 | 0.16 |
| 1M_40° C./75% RH | 0.26 | 0.17 | 0.39 |
| Assay % | | | |
| Initial | 101.5 | 101.1 | 103.1 |
| 1 M 2-8° C. | 101.1 | 99.7 | 102.6 |
| 1M_25° C./60% RH | 101.1 | 100.2 | 102.4 |
| 1M_40° C./75% RH | 100.8 | 100.6 | 102.1 |

Manufacturing Process:
1. 90% batch quantity of water for injection was collected in a vessel.
2. Batch quantity of sodium chloride was added and dissolved under stirring.
3. Batch quantity of disodium edetate was added and dissolved under stirring.
4. pH was checked and adjusted to pH 2.7 using 1N HCL solution.
5. Batch quantity of Tiotropium Bromide was added and dissolved under stirring.
6. Volume of bulk was made up.

Example 5

The below example illustrates the compositions with different pH adjusting agents such as citrate buffer and 1 N HCl

| Sr. No. | Ingredients | 5A mcg/2 ml | 5A % w/w | 5B mcg/2 ml | 5B % w/w |
|---|---|---|---|---|---|
| 1 | Tiotropium Bromide anhydrous eq. to tiotropium | 80 | 0.004 | 80 | 0.004 |
| 2 | Disodium EDTA | 20 | 0.001 | 20 | 0.001 |
| 3 | Sodium chloride | 18000 | 0.9 | 18000 | 0.9 |
| 4 | Citric acid monohydrate | 8000 | 0.40 | — | — |
| 5 | Sodium citrate dihydrate | 1200 | 0.06 | — | — |
| 6 | 1N HCl | — | | q.s. to pH 2.7 | |
| 7 | Water for injection | qs | qs | qs | qs |
| | pH of solution | 2.65 | | 2.71 | |

| Stability data | | |
|---|---|---|
| # | 5A | 5B |
| Related substances (Impurity A (2-hydroxy-2,2-dithiophen-2-ylacetic acid)) | | |
| Initial | 0.02 | ND |
| 1 M 2-8° C. | 0.03 | 0.03 |
| 1M_25° C./60% RH | 0.06 | 0.06 |
| 1M_40° C./75% RH | 0.18 | 0.16 |
| Total impurities | | |
| Initial | 0.07 | ND |
| 1 M 2-8° C. | 0.16 | 0 |
| 1M_25° C./60% RH | 0.26 | 0.09 |
| 1M_40° C./75% RH | 0.38 | 0.17 |
| Assay % | | |
| Initial | 104.9 | 101.1 |
| 1 M 2-8° C. | 104.2 | 99.7 |
| 1M_25° C./60% RH | 104.4 | 100.2 |
| 1M_40° C./75% RH | 103.5 | 100.6 |

Manufacturing Process (5A)
1. 90% batch quantity of water for injection was collected in a vessel.
2. Batch quantity of sodium chloride was added and dissolved under stirring.
3. Batch quantity of disodium edetate was added and dissolved under stirring.
4. Batch quantity of citric acid monohydrate was added and dissolved under stirring.
5. Batch quantity of sodium citrate dihydrate was added and dissolved under stirring.
6. Batch quantity of Tiotropium Bromide was added and dissolved under stirring.
7. Volume of bulk was made up.

Manufacturing Process (5B)
1. 90% batch quantity of water for injection was collected in a vessel.
2. Batch quantity of sodium chloride was added and dissolved under stirring.
3. Batch quantity of disodium edetate was added and dissolved under stirring.
4. pH was checked and adjusted to pH 2.7 using 1N HCL solution.
5. Batch quantity of Tiotropium Bromide was added and dissolved under stirring.
6. Volume of bulk was made up.

Example 6

The below example illustrates the compositions at different pH ranges.

| Sr. No | Ingredients | 6A mcg/2 ml | 6B mcg/2 ml | 6C mcg/2 ml | 6D mcg/2 ml | % w/w |
|---|---|---|---|---|---|---|
| 1 | Tiotropium Bromide anhydrous eq. to tiotropium | 80 | 80 | 80 | 80 | 0.004 |
| 2 | Disodium EDTA | 20 | 20 | 20 | 20 | 0.001 |
| 3 | Sodium chloride | 18000 | 18000 | 18000 | 18000 | 0.9 |
| 5 | 1N HCl | q.s. to pH 2.7 | q.s. to pH 2.9 | q.s. to pH 2.4 | q.s. to pH 2.2 | — |
| 6 | Water for injection | qs | qs | qs | qs | qs |

Stability data

| # | 6A | 6B | 6C | 6D |
|---|---|---|---|---|
| Related substances Impurity A (2-hydroxy-2,2-dithiophen-2-ylacetic acid) | | | | |
| Initial | 0.03 | 0.03 | 0.02 | 0.03 |
| 1 M 2-8° C. | 0.04 | 0.05 | 0.05 | 0.06 |
| 1M_25° C./60% RH | 0.07 | 0.09 | 0.09 | 0.12 |
| 1M_40° C./75% RH | 0.21 | 0.27 | 0.19 | 0.23 |
| Total impurities | | | | |
| Initial | 0.19 | 0.19 | 0.19 | 0.18 |
| 1 M 2-8° C. | 0.18 | 0.20 | 0.21 | 0.18 |
| 1M_25° C./60% RH | 0.20 | 0.13 | 0.23 | 0.26 |
| 1M_40° C./75% RH | 0.33 | 0.41 | 0.33 | 0.35 |
| Assay % | | | | |
| Initial | 97.9 | 102.5 | 103.1 | 102.8 |
| 1 M 2-8° C. | 95.6 | 102.30 | 102.2 | 102.2 |
| 1M_25° C./60% RH | 95.6 | 102.3 | 101.6 | 101.9 |
| 1M_40° C./75% RH | 95.0 | 101.4 | 100.8 | 101.2 |

Manufacturing Process:

1. 90% batch quantity of water for injection was collected in a vessel
2. Batch quantity of sodium chloride was added and dissolved under stirring.
3. Batch quantity of disodium edetate was added and dissolved under stirring.
4. pH was checked and adjusted as desired using 1N HCL solution
5. Batch quantity of Tiotropium Bromide was added and dissolved under stirring.
5. Volume of bulk was made up.

Example 7

The below example illustrates compositions with different fill volumes per unit dosage form

| Sr. No. | Ingredients | 7A 80 mcg/ 1 ml | % w/w | 7B 80 mcg/ 2 ml | % w/w | 7C 80 mcg/ 3 ml | % w/w |
|---|---|---|---|---|---|---|---|
| 1 | Tiotropium Bromide anhydrous eq. to tiotropium | 80 | 0.008 | 80 | 0.004 | 80 | 0.0026 |
| 2 | Disodium EDTA | 20 | 0.002 | 20 | 0.001 | 20 | 0.0006 |
| 3 | Sodium chloride | 9000 | 0.9 | 18000 | 0.9 | 27000 | 0.9 |
| 4 | 1N HCl | | | q.s. to pH 2.7 | | | |
| 5 | Water for injection | q.s 1 ml | | q.s 2 ml | | q.s 3 ml | |
| | pH of solution | 2.69 | | 2.71 | | 2.68 | |

| # | 7A | 7B | 7C |
|---|---|---|---|
| Related substances Impurity A (2-hydroxy-2,2-dithiophen-2-ylacetic acid) | | | |
| Initial | ND | ND | ND |
| 1 M 2-8° C. | 0.01 | ND | ND |
| 1M_25° C./60% RH | 0.04 | 0.09 | 0.04 |
| 1M_40° C./75% RH | 0.15 | 0.17 | 0.15 |
| Total impurities | | | |
| Initial | 0.09 | 0 | 0 |
| 1 M 2-8° C. | 0.11 | 0.16 | 0 |
| 1M_25° C./60% RH | 0.17 | 0.19 | 0.04 |
| 1M_40° C./75% RH | 0.29 | 0.28 | 0.15 |
| Assay % | | | |
| Initial | 103.2 | 102.9 | 104.1 |
| 1 M 2-8° C. | 102.9 | 102.7 | 103.4 |
| 1M_25° C./60% RH | 101.8 | 101.8 | 102.1 |
| 1M_40° C./75% RH | 100.9 | 102.1 | 101.4 |

Manufacturing Process:

1. 90% batch quantity of water for injection was collected in a vessel.
2. Batch quantity of sodium chloride was added and dissolved under stirring.
3. Batch quantity of disodium edetate was added and dissolved under stirring.
4. pH was checked and adjusted to pH 2.7 using 1N HCL solution.
5. Batch quantity of Tiotropium Bromide was added and dissolved under stirring.
6. Volume of bulk was made up.

Although the invention herein has been described with reference to particular embodiments, it is to be understood that these embodiments are merely illustrative of the principles and application of the present invention. It is therefore to be understood that numerous modifications may be made to the illustrative embodiments and that other arrangements may be devised without departing from the spirit and scope of the present invention as described.

We claim:

1. A pharmaceutical composition comprising
   (i) about 0.0001% to about 0.03% by weight of tiotropium or a pharmaceutically acceptable salt thereof;
   (ii) water;
   (iii) a complexing agent, the complexing agent being disodium EDTA and present at a concentration of up to 0.01% by weight,
   wherein (a) the composition is free of preservative, (b) the composition is in a solution form for nebulization, (c) the tiotropium or pharmaceutically acceptable salt thereof is the sole active ingredient in the composition, and (d) the osmolality of the composition is 275 mOsm/kg to 325 mOsm/kg.

2. A composition according to claim 1, wherein tiotropium is present in an amount of about 0.001 mg to about 0.3 mg.

3. A composition according to claim 1, wherein tiotropium is present in an amount of about 0.005 mg to about 0.2 mg.

4. A composition according to claim 1, wherein the complexing agent is present in an amount of about 0.01% by weight.

5. A composition according to claim 1, wherein the composition further comprises sodium chloride.

6. A composition according to claim 5, wherein the sodium chloride is present in an amount up to about 0.9% by weight.

7. A composition according to claim 1, wherein the composition is contained in a prefilled container.

8. A composition according to claim 1, wherein the volume of the composition is between about 0.1 ml to about 5 ml.

9. A composition according to claim 1, wherein the pH of the composition is between about 2.5 to about 3.5.

10. A composition according to claim 9, wherein the pH of the composition is about 2.7.

11. A kit comprising a nebulizer, instructions for using a nebulizer and the composition according to claim 1.

12. A method of relieving bronchospasm associated with chronic obstructive pulmonary disease in a patient comprising administering to said patient the composition according to claim 1.

13. A process of preparing a pharmaceutical composition comprising about 0.0001% to about 0.03% by weight of tiotropium or a pharmaceutically acceptable salt thereof, water, about 0.01% by weight of a complexing agent, and about 0.9% by weight of sodium chloride, wherein the composition has a pH ranging from about 2.7 to about 2.9 and is free of preservative, the process comprising the steps of:
  (a) dissolving sodium chloride in water to form a solution;
  (b) adding a complexing agent to the solution of step (a);
  (c) adjusting the pH of the solution of step (b) to about 2.7 to about 2.9;
  (d) adding tiotropium or a pharmaceutically acceptable salt thereof;
  (e) filtering the solution of step (d); and
  (f) filling a container with the solution of step (e).

14. A prefilled container containing about 2 mL of an aqueous pharmaceutical composition comprising (i) from about 10 to about 80 µg of tiotropium bromide;
  (ii) sodium chloride; and
  (iii) about 0.01% by weight of disodium EDTA, wherein the composition is free of preservative, and the composition has a pH of from about 2.7 to about 2.9.

15. The prefilled container of claim 14, wherein the sodium chloride is present at about 0.9% by weight.

16. The prefilled container of claim 15, wherein the pH of the pharmaceutical composition is about 2.7.

17. The process of claim 13, wherein the osmolality of the composition is 275 mOsm/kg to 325 mOsm/kg.

18. The prefilled container of claim 14, wherein the osmolality of the pharmaceutical composition is 275 mOsm/kg to 325 mOsm/kg.

19. The composition of claim 6, wherein (a) the complexing agent is present in an amount of about 0.01% by weight, (b) the composition comprises from about 10 to about 80 µg of tiotropium bromide, (c) the volume of the composition is about 2 mL, and (d) the pH of the composition is from about 2.7 to about 2.9.

20. A method of relieving bronchospasm associated with chronic obstructive pulmonary disease in a patient comprising administering to said patient the composition according to claim 19.

* * * * *